United States Patent
Priest et al.

(10) Patent No.: US 9,802,139 B2
(45) Date of Patent: Oct. 31, 2017

(54) METHOD AND APPARATUS FOR CLEANING A FLUID

(75) Inventors: William Lawrence Priest, West Hartford, CT (US); Satish Kumar, East Lyme, CT (US); Gregory Allen Slawson, Saline, MI (US)

(73) Assignee: OIL PURIFICATION SYSTEMS, INC., Shelton, CT (US)

( * ) Notice: Subject to any disclaimer, the term of this patent is extended or adjusted under 35 U.S.C. 154(b) by 224 days.

(21) Appl. No.: 12/676,502

(22) PCT Filed: Sep. 4, 2008

(86) PCT No.: PCT/US2008/010384
§ 371 (c)(1),
(2), (4) Date: Mar. 4, 2010

(87) PCT Pub. No.: WO2009/032285
PCT Pub. Date: Mar. 12, 2009

(65) Prior Publication Data
US 2010/0219135 A1    Sep. 2, 2010

Related U.S. Application Data

(60) Provisional application No. 60/967,375, filed on Sep. 4, 2007.

(51) Int. Cl.
  *B01D 1/00*    (2006.01)
  *B01D 3/42*    (2006.01)
  (Continued)

(52) U.S. Cl.
  CPC ............. *B01D 3/42* (2013.01); *B01D 1/0082* (2013.01); *B01D 35/143* (2013.01); *G01N 25/14* (2013.01)

(58) Field of Classification Search
  CPC ...... B01D 1/0082; B01D 3/42; B01D 35/143; B01D 35/185; G01N 25/14
  See application file for complete search history.

(56) References Cited

U.S. PATENT DOCUMENTS 3,440,865 A * 4/1969 Gamson ................. G01N 25/14
                                                              202/160
4,413,674 A    11/1983 Avery et al.
(Continued)

OTHER PUBLICATIONS

PCT/ISA/220 Notification of Transmittal of the International Search Report and the Written Opinion of the International Searching Authority dated Nov. 19, 2008 for PCT/US2008/10384.
(Continued)

*Primary Examiner* — Jonathan Miller
(74) *Attorney, Agent, or Firm* — Dilworth IP LLC

(57) ABSTRACT

A method and apparatus for cleaning a fluid comprising a fluid supply port for receiving a contaminated fluid; a fluid return port for providing a cleaned fluid; an evaporator for evaporating liquid contaminants from the fluid; a fluid line connecting the evaporator between the fluid supply port and the fluid return port; a sensor connected to at least one of the fluid filter, the evaporator, and the fluid line; a controller connected to an output of the sensor, wherein the controller includes: a processor; and a memory device including computer readable instructions which, when executed by the processor cause the processor to perform the steps of: receiving data from the sensor; comparing the data from the sensor to reference data; sending a control signal to at least one of the fluid filter and the evaporator based on comparing the data from the sensor to the reference data.

4 Claims, 12 Drawing Sheets

(51) Int. Cl.
*G01N 25/14* (2006.01)
*B01D 35/143* (2006.01)

(56) References Cited

U.S. PATENT DOCUMENTS

| | | | | |
|---|---|---|---|---|
| 4,528,635 | A | * | 7/1985 | Juodikis .................. B01D 3/42 374/27 |
| 4,843,833 | A | | 7/1989 | Polkinghorne |
| 5,531,801 | A | * | 7/1996 | Sewell .................. B01D 47/06 95/10 |
| 7,334,557 | B2 | * | 2/2008 | Callan .................. F01M 1/18 123/196 A |
| 7,976,702 | B2 | * | 7/2011 | Geiger ................ B01D 35/185 196/115 |
| 2004/0040789 | A1 | | 3/2004 | Rake et al. |
| 2004/0140271 | A1 | | 7/2004 | Whitmore et al. |
| 2006/0102133 | A1 | * | 5/2006 | Callan .................. F01M 1/18 123/196 R |

OTHER PUBLICATIONS

PCT/ISA/210 International Search Report dated Nov. 19, 2008 for PCT/US2008/10384.
PCT/ISA/237 Written Opinion of the International Searching Authority dated Nov. 19, 2008 for PCT/US2008/10384.
Form PCT/IPEA/409 International Preliminary Report on Patentability dated May 12, 2010, concerning International Application No. PCT/US2008/010384, 9 pages.
Form PCT/IPEA/416 Notification of Transmittal of International Preliminary Report on Patentability dated May 12, 2010, concerning International Application No. PCT/US2008/010384.
Form PCT/IPEA/401 Demand dated Jul. 2, 2009, with letter accompanying Demand, concerning International Application No. PCT/US2008/010384.

* cited by examiner

METHOD AND APPARATUS FOR CLEANING A FLUID

CROSS-REFERENCE TO RELATED APPLICATIONS

This application claims priority from International application number PCT/US2008/010384, filed Sep. 4, 2008, which claims priority from U.S. Provisional patent application No. 60/967,375, filed Sep. 4, 2007.

STATEMENT REGARDING FEDERALLY-SPONSORED RESEARCH AND DEVELOPMENT

Not Applicable.

FIELD OF THE INVENTION

The present invention is directed generally fluid cleaning and, more specifically, to methods and apparatuses for fluid cleaning and regulating those processes based on operating conditions.

BACKGROUND OF THE INVENTION

There are many methods and apparatuses that utilize fluids, such as fluids for lubricants in internal combustion engines, fluids to apply forces in hydraulic systems, and other uses of fluids. In general, it is important to keep those fluids clean and free from contaminants.

A variety of methods and apparatuses are commonly used to remove contaminants and to keep fluids clean. Filtration is the dominant method for removing solid particulates from a fluid. Removal of liquid contaminants has also spawned a significant number of technologies designed to remove them including such methods as gravity separation, centrifuge, polymer absorption, vacuum dehydration, and evaporation.

Throughout the years a number of systems have been proposed and designed utilizing both filtration and evaporation as a method for cleaning a fluid by removing solid particulates and removing liquid contaminates from the fluid. In some cases these processes are carried out in a vessel designed to perform both operations and in others it is accomplished in two chambers designed to perform the operations separately. For various reasons, either the single vessel design or the two chamber design can be argued to have an advantage over the other, yet both suffer from the same disadvantages regardless of configuration. In particular, neither has the ability to satisfactorily adapt to the changes in their environment or operating conditions.

Historically these types of systems have been dependent on mechanical means for controlling the processes of cleaning. Flow control has been accomplished through the means of a valve or a fixed orifice designed to limit flow at a predetermined set of operating characteristics for their intended application, such as pressure, temperature, flow rate, etc. Heating for the evaporation process is also limited in that the element used is sized based on the same characteristics and is wired directly to a voltage source. Although, a number of configurations for this process have been proposed, none utilize a control to adjust the flow of the fluid or output of the heating element.

Unfortunately, the environments in which these systems operate are generally not characterized by static operating characteristics. For most of these systems, the dynamic environment in which they operate presents an issue with performance due to the inability of the cleaning apparatus or system to adapt to changing conditions.

Accordingly, there is a need for a method and apparatus for fluid cleaning that includes regulating those processes based on operating conditions. Those and other advantages of the present invention will be described in more detail hereinbelow.

BRIEF SUMMARY OF THE INVENTION

The present invention applies generally to fluid cleaning methods and apparatuses. The present invention will generally be described in terms of methods and apparatuses for fluid cleaning utilizing the processes of filtration and evaporation, and regulating those processes based on data indicative of operating conditions. However, many modifications and variations are possible with the present invention, and the description and examples of the present invention are illustrative of the invention, and not limiting.

In one embodiment, the present invention includes an apparatus for cleaning a fluid including a filtration assembly, an evaporation assembly, a controller, and sensors. The present invention provides several advantages over the prior art. For example, by using sensors to detect various operating characteristics within the fluid cleaning system or a related application, the controller can be used to regulate the performance of both the filtration and evaporation processes, or other aspects of the invention, to optimize the cleaning of a fluid. The sensors can also be used to monitor the operating performance of the related application, which allows the controller to adapt and modify the fluid cleaning system performance to maintain optimized operation.

The present invention allows for easier and faster installation because a system implementing the present invention will require less adjustment and calibration during installation than prior art apparatuses (and in some cases little or no adjustment or modification will be required). As a result, the present invention allows for a reduction in the time and effort required for installation of the apparatus, thereby reducing costs.

The present invention also allows for the reduction or elimination of certain operating risks such as fluid overflow and excessive heating caused when the operating characteristics of the application change over time.

The present invention also makes it possible to provide service and diagnostic indicators, thereby improving the performance and maintenance of the system.

The present invention may include or be embodied as computer software which, when executed by a processor, causes the processor to perform certain actions according to the present invention. In one embodiment, the controller includes or is embodied as a computer or computer system, comprising a processor, memory, an input device, and an output device. The memory includes computer-readable instructions which, when executed, cause the processor to certain actions according to the present invention. The input and output devices allow for communication, such as with a person operating the apparatus. The input and output devices may also allow, for example, for the operation of the apparatus to be manually modified, for updates and enhancements of the apparatus, and for diagnostics and other trouble shooting uses. The processor can also receive input from the sensors and provide output, such as control signals, to control the operation of the apparatus.

Many variations are possible with the present invention, and these and other teachings, variations, and advantages of the present invention will become apparent from the following detailed description of the invention.

BRIEF DESCRIPTION OF THE SEVERAL VIEWS OF THE DRAWING

Embodiments of the present invention will now be described, by way of example only, with reference to the accompanying drawings for the purpose of illustrating the embodiments, and not for purposes of limiting the invention, wherein.

DETAILED DESCRIPTION OF THE INVENTION

Figure 1:
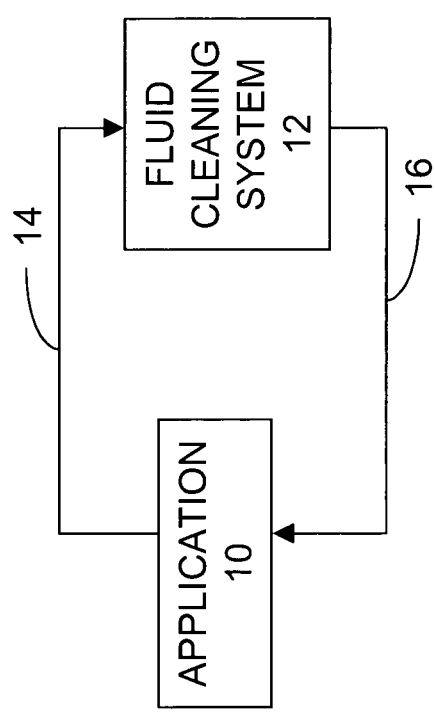
FIG. 1 is a schematic illustrating one embodiment of the system for and method of fluid cleaning as it relates to an application.

FIG. 1 is a schematic illustrating one example of the use of the present invention. In that embodiment, an application 10 is connected to a fluid cleaning system 12. Fluid from the application 10 is provided to the fluid cleaning system 12 via a supply line 14, where the fluid is cleaned as described in more detail hereinbelow. After cleaning, the fluid is returned to the application 10 via a return line 16.

The application 10 may be any mechanism or system utilizing a fluid which becomes contaminated. For example, the application 10 may be an internal combustion engine, a hydraulic system, a gearbox, or other applications. The fluid may be, for example, lubricating oil, hydraulic fluid, cooling fluid, or other fluids susceptible to contamination, such as solid particulate contamination and/or liquid contaminates. If left untreated, contaminants, both liquid and particulate, will usually reduce the usable life of the fluid and the application 10.

The fluid may be any of a wide variety of industrial fluids. Industrial fluids are used in industrial devices which often, but not always, have moving parts. Industrial fluids tend to become contaminated or to otherwise degrade with the use of the application 10. Furthermore, industrial fluids are typically recirculated through the industrial device, which results in the industrial fluid becoming more contaminated and more degraded with continued use of the application. As a result, industrial fluids must be either replaced or cleaned in order to maintain the proper operation of the application 10. Some examples of industrial fluids are lubricating oil, hydraulic fluid, cooling fluids, and others. Examples of industrial devices include internal combustion engines and gearboxes which have many moving parts and typically use both a lubricating oil and a cooling fluid, hydraulic devices which sometimes have a small number of moving parts (such as a single hydraulic piston) and which utilize hydraulic fluids, and electrical transformers which use cooling fluids and which may not have moving parts in the actual transformer, but which often include moving parts in the form of pumps to circulate the cooling fluid.

In operation, the fluid is transmitted via fluidic conductors (one or more supply lines 14) to the fluid cleaning system 12, where the fluid is cleaned of contaminates and then returned via fluidic conductors (one or more return lines 16) to the application 10. The flow of fluid between the application 10 and the cleaning system 12 may be controlled by the cleaning system 12, by the application 10, or by some other device. The fluid flow between the application 10 and the system 12 may be at the same fluid flow rate as the fluid passing through the application 10, or a lower fluid flow rate may be used. For example, the fluid cleaning system 12 may be series connected with the fluid flow in the application 10 so that all fluid flows through the fluid cleaning system 12 each time the fluid circulates through the application 10. In other embodiments, only a portion of the fluid is diverted to the fluid cleaning system 12, so that more than one trip through the application 10 is required before the entire volume of fluid is cleaned.

The fluid cleaning system 12 may be separate from the application 10 and connected to the application 10 via supply 14 and return 16 lines between the application 10 and system 12. In other embodiments, the system 12 and the application 10 may be integrated with each other. For example, the fluid cleaning system 12 may be part of the application 10. In such an embodiment, the supply 14 and return 16 lines may be parts within the integrated application 10 and fluid cleaning system 12 by which the fluid is carried to the portion of the integrated application 10 and system 12 that performs the cleaning of the fluid. In some embodiments, the cleaning system 12 may be integrated into the application 10 such that the industrial fluid is not diverted from its usual path within the application 10, but rather the cleaning system 12 is within a portion of the application 10 in which the fluid normally passes. For example, the application 10 may be an internal combustions engine and the system 12 may be located in the oil pan of the engine, or in some other part of the engine where the oil or other industrial fluid is normally present.

Figure 2:
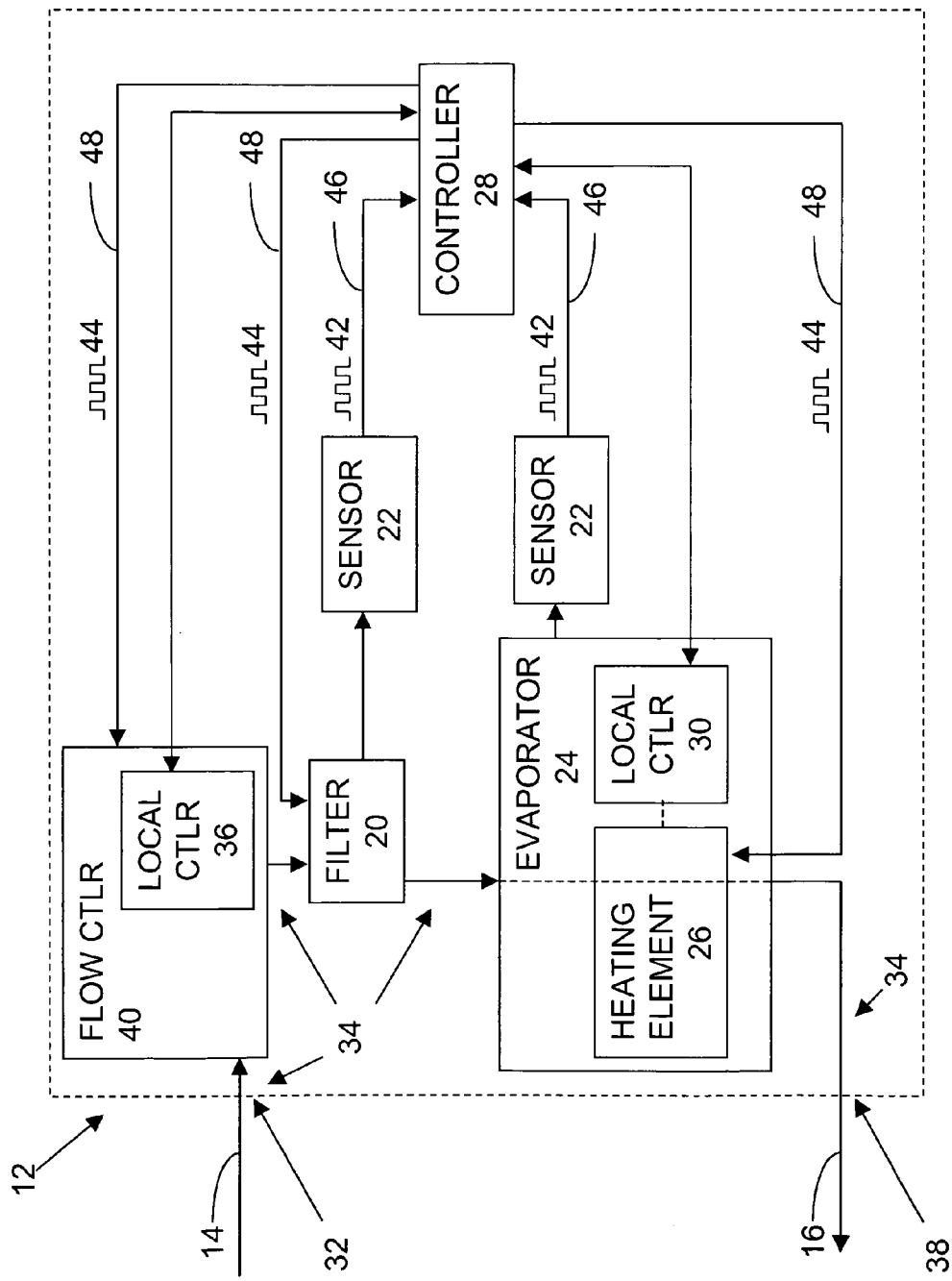
FIG. 2 is a schematic of one embodiment of the present invention illustrating the relationship between the components of the system for fluid cleaning including the filter assembly, the evaporation assembly, the controller, and the sensors.

FIG. 2 is a schematic of one embodiment of the fluid cleaning system 12 according to the present invention. The fluid cleaning system 12 including a filter 20, sensors 22, an evaporator 24, a controller 28, a supply line 14, a supply port 32, a return line 16, a return port 38, and a flow controller 40. Fluid from the application 10 is carried through a supply line 14 from the application 10 and enters the system 12 through the supply port 32. The fluid is carried through one or more fluid lines 34 through the system 12 and passes through the filter 20 and the evaporator 24 where solid and liquid contaminates are removed. The fluid exits the evaporator 24 and is returned to the application 10 via the return line 16 that connects to the system 12 via the return port 38. The filter 20 and evaporator 24 may be constructed, for example, as described in U.S. Pat. No. 7,244,353, issued to Whitmore et al., and entitled "Method of and System for Fluid Purification". Other constructions for the filter 20 and evaporator 24 are also possible with the present invention.

The filter 20 may be, for example, a conventional filter or filter medium for removing solid particulates from the fluid. The filter 20 may be an in-line filter or it may be part of a larger filtration chamber or assembly.

The sensors 22 can consist of one or more sensing technologies designed to measure flow, pressure, fluid level, temperature, and other characteristics. The sensors 22 may capture and transmit data in digital form or analog form. In some embodiments, some of the sensors 22 are analog and others are digital. The data signals 42 from the sensors 22 are transmitted to the controller 28 for further processing as described in more detail herein. In some embodiments, the data signals 42 from one or more of the sensors 22 may be transmitted to one or more local controllers 30, 36. Sensors 22 may, for example, be located in positions to measure operating characteristics of the system 12, such as by monitoring characteristics at the filter 20 and the evaporator 24, as well as at other locations. The sensors 22 may be used at other locations within and outside of the system 12. For example, sensors 22 may be used to measure characteristics at the supply and return lines 14, 16 and ports 32, 38. Sensors 22 may be used to measure characteristics at the heating element 26 and the fluid flow controller 40. Sensors 22 may also be located in or near the application 10 and in other locations. In one embodiment, sensors 22 measure characteristics of the application 10 to better control the operation of the system 12, such as by measuring fluid temperature, pressure, flow rate and other parameters in the application 10. The number, type, and location of sensors 22 will vary depending on the particular embodiment and application of the present invention.

The evaporator 24 includes a heating element 26 to heat the fluid passing through the heating element 26 and thereby remove certain contaminants within the fluid. Typically, liquid contaminants are removed through evaporation in the evaporator 24, and the evaporated contaminants are typically vented out of the evaporator 24. The heating element 26 can be controlled by the controller 28. As will be discussed in more detail hereinbelow, the heating element 26 can be controlled in response to one or more characteristics in the system 12, such as fluid flow, fluid level, fluid pressure, fluid temperature, and other characteristics.

The evaporator 24 may also include a local controller 30 which may communicate with the controller 28 to provide, for example, diagnostic information about the evaporator 24 as well as other data such as the temperature profile and other data. For example, the evaporator 24 may include heating element control logic and drivers which provide data to the controller 28 and which receive control signals from the controller 28. In other embodiments, the evaporator 24 may have a local controller 30 to perform other tasks or no local controller 30.

The local controller 30 may communicate with the controller 28 via data signal lines 46 and control signal lines 48, or via other communication lines. The communication between the controller 28 and the local controller 30 may be bi-directional such that signals are sent from the local controller 30 to the controller 28 and from the controller 28 to the local controller 30. For example, the local controller 30 may send data to the controller 28 and the controller 28 may send control signals to the local controller 30. In other embodiments, the communication may be in only one direction. For example, the local controller 30 may only receive signals from the controller 28, and the controller 28 may receive data from sources other than the local controller 30. Similarly, the controller 28 may only receive data from the local controller 30 and may not send control signals or data to the local controller 30.

The local controller 30 may operate the evaporator (e.g., the heating element 26) directly, or the local controller 30 may receive instructions from the controller 28 or from other devices. For example, the local controller 30 may perform diagnostic tests on the evaporator and determine how to operate the evaporator 24, or the local controller 30 may rely on control signals from the controller 28 for the operation of the evaporator 24. In some embodiments, the local controller 30 may receive data signals 42 directly from one or more sensors 22. In other embodiments, sensor 22 data signals 42 are provided to the controller 28, and the controller 28 determines what information is provided to the local controller 30.

The local controller 30 may be similar in design to the controller 28 and may include, for example, a processor, memory, input and output devices. and other components. The memory may include computer-readable instructions which cause the process of the local controller 30 to perform the operations described herein.

The controller 28 monitors and controls the fluid cleaning process. The controller 28 receives data signals 42 from the sensors 22 and provides control signals 44 for the proper operation of the system 12. The data signals 42 and the control signals 44 may be transmitted over data signal lines 46 and control signal lines 48, respectively. The data signal lines 46 and control signal lines 48 may be, for example, electrical conductors such as wires, optical media such as optical fiber, and wireless media such as electromagnetic waveguides or ambient air between the sensors 22 and the controller 28. In some embodiments, the controller 28 may utilize one or more separate receivers and transmitters (not shown) for receiving and transmitting the data signals 42 and control signals 44 which are then transmitted between the transmitters/receivers (not shown) and the controller 28.

The controller 28 may also include service and diagnostic capability and may provide that functionality through either on-board displays or as an output to an external display device. Based on inputs from the sensors 22, the controller 28 will generate control signals 44 to regulate operational characteristics, such as flow, temperature, fluid level, pressure, and other characteristics, to facilitate and optimize the cleaning process. The controller 28 may, for example, operated on discrete logic, specific algorithms, or a combination of both. The controller 28 may be an integrated device or it may be made from discrete components, and the controller 28 may include or be embodied as hardware, software, firmware, and combinations thereof. The controller is described in more detail hereinbelow with reference to FIG. 3.

The controller 28 may be centrally located or it may be distributed. For example, the controller 28 may be located in a single location and receive data signals and send control signals to other parts of the system 12. In other embodiments, the controller 28 may be distributed in the form of several controllers, such as a main controller 28 and one or more local controller 30, 36 which may be collectively referred to as a controller 28.

The supply line 14 and the return line 16 connect the system 12 to the application 10. For example, the system 12 may be a separate unit connected to the application 10 via the fluid lines 14, 16. In other embodiments, the fluid lines 14, 16 may be eliminated and the system 12 may be integrated into the application 10. Although FIG. 2 illustrates one supply line 14 and one return line 16, the present invention may include more than one supply line 14 and more than one return line 16.

The supply port 32 and the return port 38 are the interfaces where the fluid enters and exits the system 12. In some embodiments the supply and return ports 32, 38 are used to connect supply and return lines 14, 16 to the system 12. In other embodiments, such as when the system 12 is integrated with the application 10, and the supply and return ports 32, 38 are the places where the fluid enters the system 12. For example, if the system 12 is integrated with the application 10, the supply port 32 may be the input to the flow controller 40 and the return port 38 may be the output of the evaporator 24. Of course, if the components of the system 12 are rearranged, such as by removing the flow controller 40, then the supply port 32 may be the input of another component, such as the input of the filter 20 or the input of some other component. Likewise, the return port 38 may be the output of a component other then the evaporator 24 in some embodiments. Although FIG. 2 illustrates one supply port 32 and one return port 38, the present invention may include more than one supply port 32 and more than one return port 38.

The fluid lines 34 in the system 12 connect certain components of the system 12 to each other and to the supply and return ports 32, 38. Although FIG. 2 illustrates the fluid line 34 connecting the flow controller 40, filter 20, and evaporator 24 in series, the present invention may include two or more parallel fluid lines 34 connecting some or all of the components in parallel, or providing parallel redundant components. For example, the system 12 may include two parallel fluid lines 34 between the supply port 32 and the return port 38, with one of the fluid lines 34 connecting the filter 20 between the supply port 32 and the return port 38, and the other fluid line 34 connecting the evaporator 24 between the supply port 32 and the return port 38. The parallel fluid lines 34 may each be connected to a separate supply port 32, or they may share a single supply port 32. For example, the two fluid lines 34 may both connect to the output of the flow controller 40. In this embodiment, fluid passes through only one of the filter 20 and evaporator 24 each time through the system 12. As a result, fluid requires more than one pass through the system 12 to pass through both the filter 20 and the evaporator 24. In another embodiment, redundant components are provided on separate, parallel fluid lines 34 so that, if a malfunction is detected, the affected components and fluid lines 34 can be disabled or bypassed, such as with additional fluid flow controllers 40, in favor of a separate and operational component or fluid line 34. Other variations are also possible.

The system 12 may operate in different modes at different times. For example, the system 12 may have an operational mode and a diagnostic mode, as will be discussed in more detail hereinbelow with regard to FIGS. 7 and 8. Other modes are also possible with the present invention.

In one embodiment of the present invention, the controller 28 monitors the operating characteristics of the system 12 and/or the application 10, and makes appropriate changes in order to provide improved operation. For example, if the controller 28, via the sensors 22 and data signals 42, detects an undesired operating condition, the controller 28 provides control signals 44 to compensate for that undesired condition, such as by changing fluid flow through the system 12, changing the temperature of the heating element 26, changing the fluid pressure, changing the level of the fluids such as by adding fluid from a reservoir (not shown) or by removing fluid from the system 12 and placing it into a reservoir (not shown), or other changes. For example, the controller 28 can receive data signals 42 from one or more of the sensors 22, compare the data signals with "reference data", and send control signals based on the results of comparing the data signals to the reference data. The reference data may be data indicative of one or more parameters or operating conditions of the system, such as a desired value, a desired range of values for a parameter, more than one value, more than one range of values, or combinations thereof. The reference data may relate to fluid temperature, fluid pressure, fluid flow rate, heating element temperature, rate of change of any of the parameters, as well as other data. The reference data may be stored in the controller 28 or the reference data may be stored external to the controller 28, as will be described in more detail with regard to FIG. 3.

In one embodiment, the controller 28 monitors the temperature of the fluid in the evaporator 24. If that temperature is too high, then the controller 28 sends a control signal to reduce the power to the heating element 26, and if the temperature is too low the controller 28 sends a control signal to increase the power to the heating element 26.

In another embodiment, the controller 28 monitors whether the temperature change of fluid in the evaporator 24 corresponds with expected changes in the temperature of fluid in the evaporator 24. For example, if power to the heating element 26 is increased, the fluid in the evaporator 24 will also be expected to increase. If, however, the temperature of fluid in the evaporator 24 does not show the expected temperature increase (or range of values), then the system 12 may determine that a malfunction or an unexpected condition has occurred and may take corrective action.

In another embodiment, the controller 28 monitors the fluid flow rate. If the flow rate is not within an expected range of values, the controller 28 will send a control signal to one or more fluid flow controllers 40 to adjust the fluid flow rate. For example, if a flow controller 40 in the form of a valve is opened or closed, the controller 28 may determine whether the resulting fluid flow rate corresponds with the expected fluid flow rate. If the sensed fluid flow rate is not within the expected range, the controller 28 may take further corrective action. Similarly, if the fluid flow controller 40 is in the form of a pump, the controller 28 may determine whether the resulting fluid flow rate corresponds with the expected fluid flow rate and the controller 28 may take further corrective action if the sensed fluid flow rate is not within the expected range. In other embodiments of the present invention other parameters are sensed, compared to corresponding reference data, and control signals are generated in response to the sensed data and the corresponding reference data.

If the controller 28 determines that a malfunction or an unexpected condition is occurring, the controller 28 may take action to compensate for the malfunction or unexpected condition. For example, the controller 28 may increase or decrease power to the heating element 26 more or less than would normally be required in order to compensate for a faulty heating element 26. Similarly, the controller 28 may send control signals to open or close a valve 40 or increase or decrease the speed of a fluid pump 40 more or less than would normally be required in order to compensate for a faulty fluid flow controller 40 or to compensate for a condition in a different part of the system that is affecting the fluid flow rate. Other measures may also be performed by the controller 28 to compensate for detected malfunctions or unexpected conditions. For example, the controller 28 may disable part of all of the system 12 if a malfunction is detected which would cause a significant safety risk, such as a risk of a fire, a risk of a fluid line rupture, or a risk of disabling the application 10. For example, the controller 28 may disable the heating element 26 but allow fluid to continue to flow through the system 12 so that fluid continues to receive the benefit of the filter 20 even if the evaporator 24 is not operating. In other situations, different parts of the system 12 may be disabled or the entire system 12 may be disabled.

Other parameters may also be sensed and checked against reference data, and the present invention may have more or fewer devices than are illustrated in the figures. For example, the system 12 may includes more or fewer sensors 22 and control signals 44, and they may be in locations other than those shown in the figures.

The controller 28 can also learn from the particular application 10 with which it is operating. For example, each application 10 is slightly different, and the controller 28 can enter a mode of operation by which it monitors its operation and, based on the sensor 22 data signals 42, determines the system's 12 and/or the application's 10 baseline operational characteristics. As a result, the system 12 makes adjustments to compensate for the particular application 10 with which the system 12 is working and to bring the operation characteristics of the system 12 and/or the application 10 into a desired range. As a result, the present invention allows for quicker and easier installation of the system 12 because time previously required for calibration of the system 12 is reduced or eliminated because of the ability of the system 12 to learn and adjust.

The fluid supply flow may be pressurized by a pump integral to the application 10, or by a pump external of the application 10. This pump may be the fluid flow controller 40, or it may be in addition to the fluid flow controller 40. For example, the application 10 may have a fluid flow pump that pressurizes the fluid, and the system 12 may have a fluid flow controller 40 that is in the form of a valve to control the fluid flow through the system 12. The operation of this pump and control of the fluid pressure may be controlled by the application 10 or it may be controlled independent of the application 10 (such as by the system 12).

The fluid flow controller 40 controls the flow of fluid through the system 12. The fluid flow controller 40 may be, for example, a valve that controls the flow of pressurized fluid, a pump to control the flow of fluid through the system 12, or other devices for controlling the flow of fluid through the system 12. The fluid flow controller 40 may include one fluid flow device (such as one valve or one pump to control the flow of fluid) or it may contain more than one fluid flow device. For example, the fluid flow controller 40 may include more than one valve or pump to allow for a greater range of fluid flow by operating one or more than one valve or pump. Also, the fluid flow controller 40 may include one or more primary valve or pump and one or more backup valve or pump to be used if the primary valve or pump fails a diagnostic test or is otherwise not operating properly.

The fluid flow controller 40 may be controlled by the controller 28. The fluid flow controller 40 may be driven by the controller 28 based on inputs from one or more sensors 22 in the system 12. For example, valves in the fluid flow controller 40 may be opened or closed to control the rate of fluid flow through the system 12 and, thereby, to control the temperature of fluid in the evaporator 24 or to control the fluid level. The fluid flow controller 40 may also be controlled to control other aspects of the system 12. Although the fluid flow controller 40 is illustrated in FIG. 2 as being inside the system 12, the fluid flow controller 40 can also be located at other locations. For example, the fluid flow controller 40 may also be located outside of the system 12, such as in the supply 14 and return lines 16 between the system 12 and the application 10, or in the application 10. Also, more than one fluid flow controller 40 may be used for additional control of the fluid flow.

The fluid flow controller 40 may also include a local controller 36 which may communicate with the controller 28 to provide, for example, diagnostic information about the fluid flow controller 40 as well as other data. For example, the fluid flow controller 40 may include control logic and drivers which control the fluid flow controller 40, such as for controlling a valve or pump, provide data to the controller 28, and receive control signals from the controller 28. In other embodiments, the fluid flow controller 40 may have a local controller 36 to perform different tasks or no local controller 36.

The local controller 36 may operate the fluid flow devices (e.g., valves and pumps) directly, or the local controller 36 may receive instructions from the controller 28 or from other devices. For example, the local controller 36 may perform diagnostic tests on the fluid flow controller 40 and determine how to operate the fluid flow controller 40, or the local controller 36 may rely on control signals from the controller 28 for the operation of the fluid flow controller 40.

The local controller 36 may communicate with the controller 28 via data signal lines 46 and control signal lines 48, or via other communication lines. The communication between the controller 28 and the local controller 36 may be bi-directional such that signals are sent from the local controller 36 to the controller 28 and from the controller 28 to the local controller 36. For example, the local controller 36 may send data to the controller 28 and the controller 28 may send control signals to the local controller 36. In other embodiments, the communication may be in only one direction. For example, the local controller 36 may only receive signals from the controller 28, and the controller 28 may receive data from sources other than the local controller 36. Similarly, the controller 28 may only receive data from the local controller 36 and may not send control signals or data to the local controller 36. In some embodiments, the local controller 30 may receive data signals 42 directly from one or more sensors 22. In other embodiments, sensor 22 data signals 42 are provided to the controller 28, and the controller 28 determines what information is provided to the local controller 30.

The local controller 36 of the fluid flow controller 40 may be similar in design to the controller 28 and may include, for example, a processor, memory, input and output devices. and other components. The memory may include computer-readable instructions which cause the process of the local controller 36 to perform the operations described herein.

Many variations are possible with the system 12, and the figures are illustrative and not limiting, and the system 12 is not limited to the particular orientation and number of elements. For example, the system 12 may include more than one fluid flow controller 40, or the system 12 may not include any fluid flow controllers 40. In the later embodiment, for example, the system 12 may rely on fluid flow controllers 40 external to the system 12, or the fluid flow rate may be unregulated in some applications. Similarly, the system 12 may include more than one filter 20, or it may not have any filters 20. In the later embodiment, for example, the evaporator 24 may provide for sufficient cleaning for some applications or a filter may be provided external to the system 12. Similarly, the present invention may include more than one evaporator 24 and/or more than one heating element 26 in each evaporator 24. In other embodiments, the system 12 may not include any evaporators 24 and the filter 20 may be sufficient for some applications or an evaporator 24 may be provided external to the system 12. Similarly, the present invention may include more or fewer sensors 22 than illustrated in the figures, and the sensors 22 may be located in positions other than that illustrated in the figures. The system 12 may also include more than one controller 28, and the controller 28 may produce more or fewer control signals 44 than are illustrated. There may also be more than one supply line 14 and supply port 32 entering the system 12, more than one return line 16 and return port 38 from the system 12, and more than one fluid line 34 carrying fluid through the system 12. Furthermore, although the filter 20 and the evaporator 24 are illustrated as being in series with each other, it is also possible for the filter to be in parallel with the evaporator 24. Also, although the filter 20 is shown upstream from the evaporator 24, it is also possible for the evaporator 24 to be upstream from the filter 20. However, some advantages may be realized by placing the filter 20 upstream from the evaporator 24 in order to remove solid contaminants from the fluid before the fluid enters the evaporator 24. Other variations and modifications are also possible. Also, although the illustrated embodiment shows local controllers 30, 36 in the evaporator 24 and fluid flow controller 40, other parts of the system 12 may also include local controllers.

Figure 3:
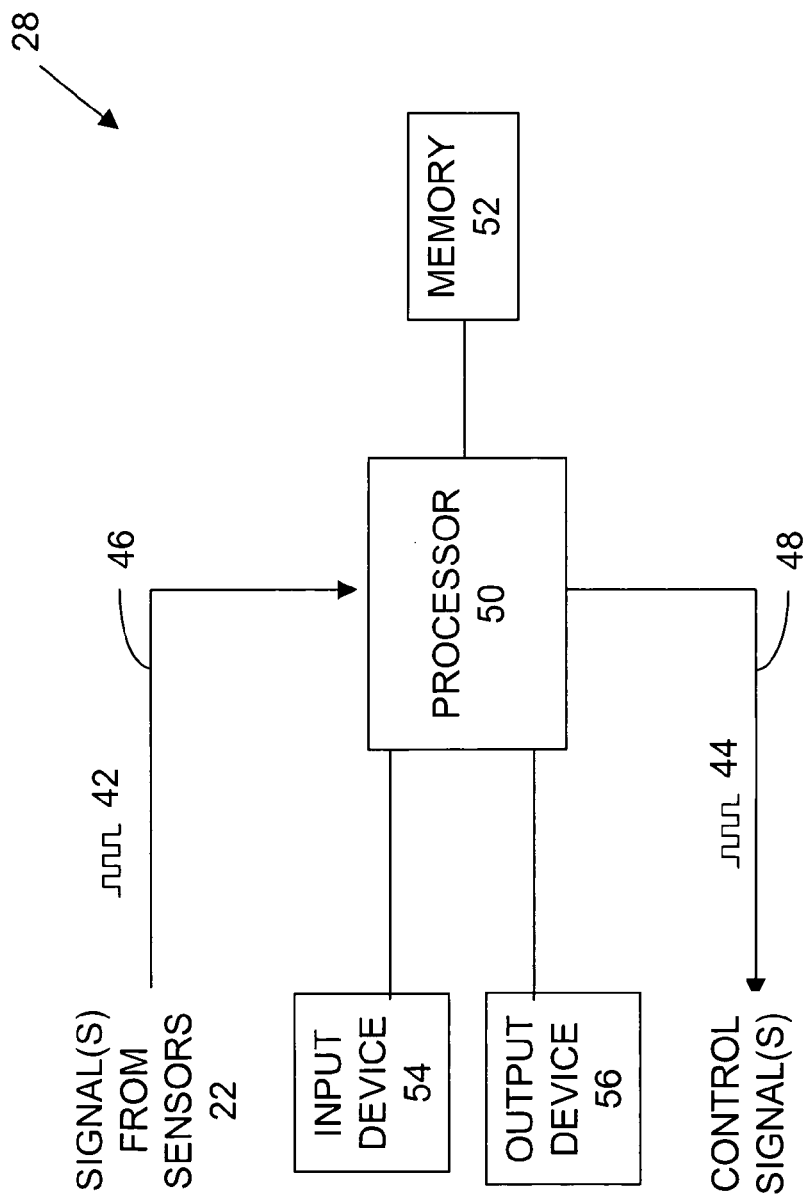
FIG. 3 is a schematic of one embodiment of a controller according to the present invention.

FIG. 3 illustrates one embodiment of a controller 28 according to the present invention. In that embodiment, the controller 28 includes a processor 50, memory 52, an input device 54, and an output or display device 56, such as a monitor. The processor 50 is connected to the memory 52, the input device 54, and the output device 56. The memory 52 includes computer readable instructions, such as computer hardware, software, firmware, or other forms of computer-readable instructions which, when executed by the processor 50, cause the processor 50 to perform certain functions, as described herein.

The processor 50 receives input from the input device 54, provides signals to control the output device 56, receives input signals 42 from the sensors 22, and provides control signals 44 to other parts of the system 12 or to parts outside of the system 12. For example, the processor 50 may change operating characteristics of the system 12 by sending control signals 44 to the evaporator 24 or to other parts of the system 12. In one example, the processor 50 may change the temperature of evaporator 24 by increasing or decreasing power to the heating element 26. In another example, the processor 50 may control the fluid flow controllers 40 or otherwise change the flow rate of fluid through the system 12. The processor 50 may also perform other functions and send other control signals 44, as described herein.

The memory 52 can be any form of computer-readable memory, and may store information in magnetic form, optical form, or other forms. The memory includes computer readable instructions which, when executed by the processor 50, cause the processor 50 to perform certain functions, as described herein. The memory 52 may also include the reference data. The memory 52 may be separate from the processor 50, or the memory 52 may be integrated with the processor 50. The memory 52 may also include more than one memory device, which may be integrated with the processor 50, separate from the processor 50, or both. The memory 52 may include, for example, both volatile memory and non-volatile memory for use as needed.

The input device 54 may be a keyboard, a touchscreen, a computer mouse, or other forms of inputting information from a user. The input device may, for example, allow an operator to change operational characteristics of the system 12, to provide input for later use (such as notations of conditions when a particular event occurs), and other input. The input device may also be used for maintenance, trouble shooting, and other diagnostic functions, as well as to provide updates and changes to the systems.

The output device 56 may be a video display or other forms of outputting information to a user. For example, the output device 56 may display information and warning about the system 12, such as the current operational state of the system, a notice when maintenance is required, a warning when an unsafe or otherwise undesirable operating condition exists, and providing information for maintenance, trouble shooting, and other diagnostic functions.

The controller 28 is not limited to the illustrated embodiment. For example, the controller 28 may include more than one processor 28, more than one memory device 52, more than one input device 54, more than one output device, no input device 54, and no output device 54. Also, the controller 28 may be connected to more than one data signal line 46, may be connected to more than one control signal line 48, may receive more than one signal 42 from the sensors 22, and may provide more than one control signals 44.

Figure 4:
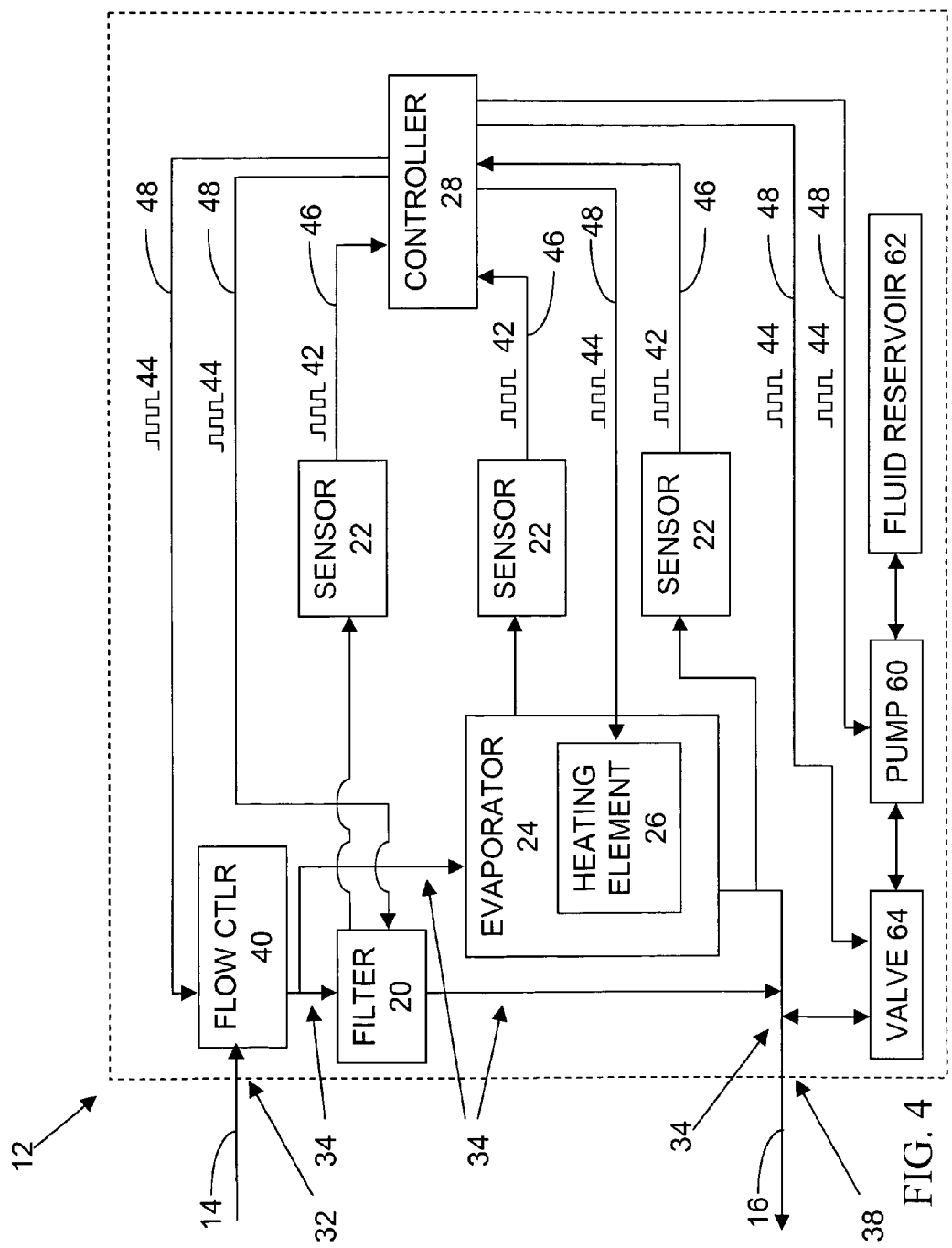
FIGS. 4 and 5 illustrate other embodiments of the system according to the present invention.

FIG. 4 illustrates another embodiment of the system 12. In that embodiment, there are two parallel fluid lines 34, with the filter 40 in one of the fluid lines 34 and the evaporator 24 in the other fluid line 34.

FIG. 4 also illustrates a pump 60 and a fluid reservoir 62 connected to the fluid line 34 via a valve 64. Control signal lines 48 connected between the controller 28 and both the valve 64 and the pump 60 allow the controller 50 to open and close the valve 64 and to control the pump 60 so as to add and remove fluid from the system 12. In this way, the fluid level may be controlled. For example, the fluid level may be reduced by moving fluid from the fluid lines 34 to the reservoir 62. Conversely, the fluid level may be increased by moving fluid from the reservoir 62 to the fluid lines 34. In other embodiments the pump 60 and reservoir 62 may be connected at a different location along the fluid line 34 or they may be connected at a location other than the fluid line 34. For example, the pump 60 and reservoir 62 may be connected via the valve 64 at the evaporator 24, the filter 20, the supply line 14, the return line 16, or at other locations in the system 12. The fluid level may be controlled in response to data from one or more sensors 22, such as a sensor 22 for detecting the fluid level in the evaporator 24 so as to control the fluid level and prevent fluid from overflowing the evaporator 24. Sensors in other locations and the control of the fluid level for other purposes is also possible with the present invention.

One or more sensors 22 may also be used to provide data regarding the fluid level to the controller 28, and the controller may use the data from the sensor 22 to determine whether to add fluid or to remove fluid from the fluid lines 34. In the illustrated embodiment, one sensor 22 is connected to the fluid line 34 after the output of the evaporator 24, although the sensor 22 may also be connect to other parts of the system 12, such as before the evaporator 24, inside the evaporator 24, before, after, or inside the filter 20, or at other places in the system 12. In other embodiments, more than one sensor 22 may be used. The use of the valve 64, pump 60, and reservoir 62 is not limited to the illustrated embodiment, and the valve 64, pump, 60 and reservoir 62 may also be used in other embodiments of the system 12, such as in embodiments in which the filter 20 and evaporator 24 are in series, in embodiments where redundant filters 20 and evaporators 24 are used, and in other embodiments.

Figure 5:
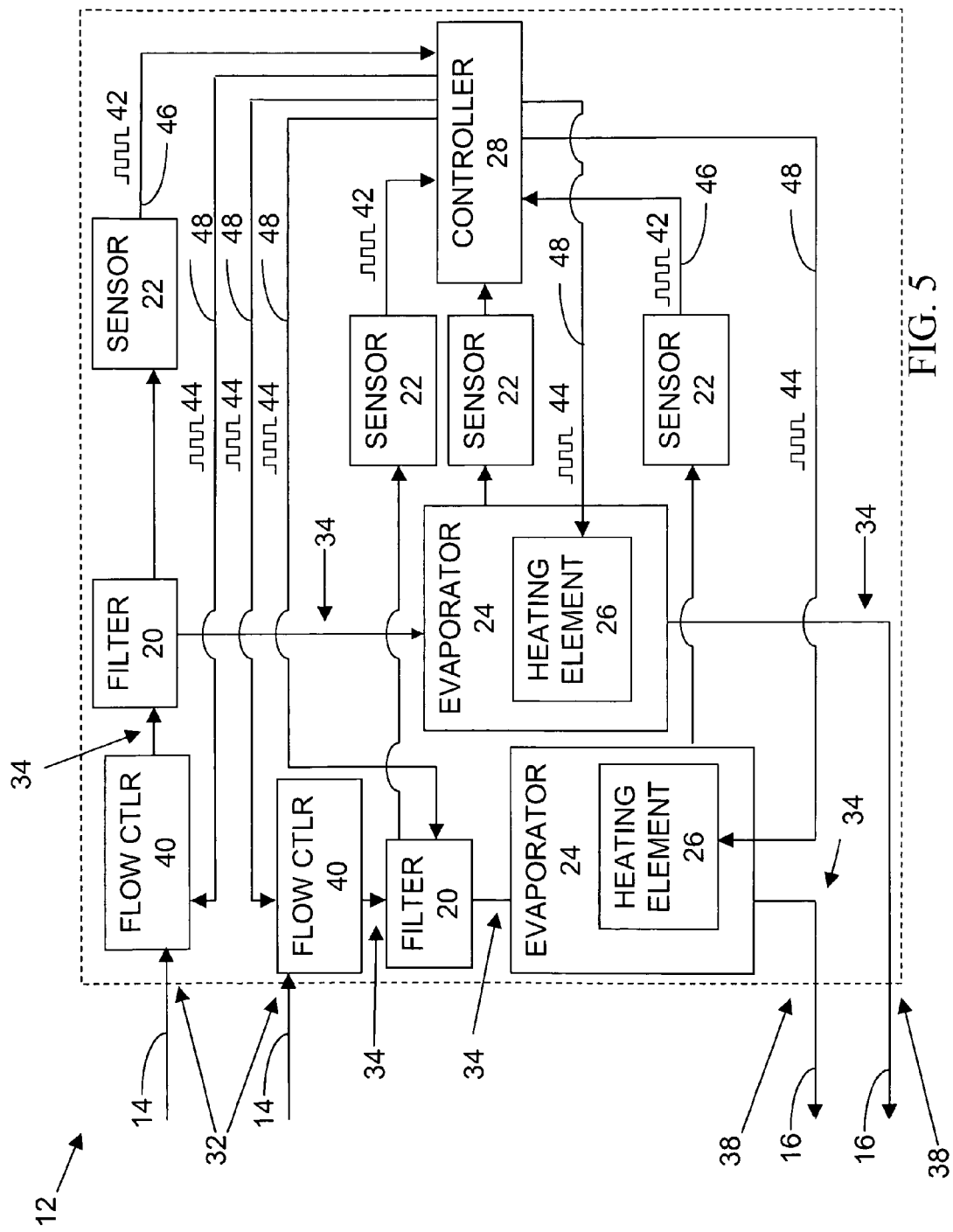

FIG. 5 illustrates another embodiment of the system 12. In that embodiment, there are two parallel fluid lines 34, with a filter 20 and an evaporator 24 in each of the parallel fluid lines. There are also two supply lines 14, two supply ports 32, two return lines 16 and two return ports 38. There are also two fluid flow controllers 40, one connected to each of the supply ports 32. The two fluid flow controllers 40 allow for separate control of fluid through the two sets of filters 20 and evaporators 24. As a result, fluid may flow through only one set of filter 20 and evaporator 24 until a malfunction is detected, at which point fluid flow to the malfunctioning filter 20 and evaporator 24 may be stopped and the fluid routed through the other filter 20 and the other evaporator 24. In other embodiments one supply line 14, one supply port 32, one return line 16, and one return port 38 may be shared and the fluid may still be controlled as described above with the use of two fluid flow controllers 40. In other embodiments, fluid may be allowed to flow through all filters 20 and evaporators 24 at the same time in order to allow for a more fluid to be cleaned. Other variations are also possible.

Figure 6:
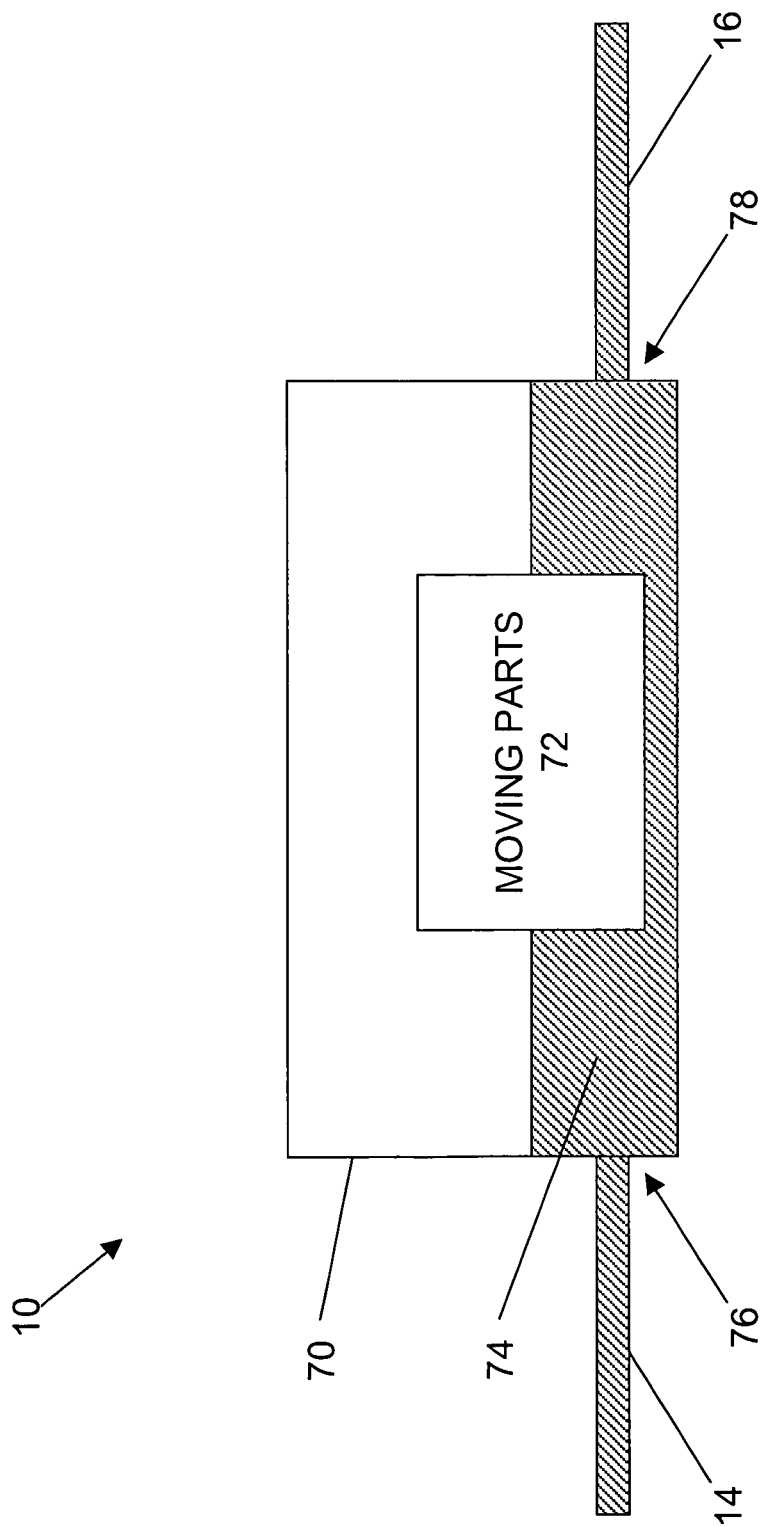
FIG. 6 illustrates one embodiment of an application according to the present invention.

FIG. 6 illustrates one embodiment of the application 10 according to the present invention. The application 10 may be an internal combustion engine, a gearbox, a hydraulic device, or other devices. The application 10 includes a housing 70 and may include one or more moving parts 72. The housing also includes the fluid 74 within the housing 70, a fluid supply port 76 in the housing 70, and a fluid return port 78 in the housing 70. Although the application 10 illustrated in this figure includes moving parts 72 and the industrial fluid 74 may be, for example, a lubricant for the moving parts, according to other embodiments of the present invention, the application 10 may not have moving parts 72 and the industrial fluid 74 may be, for example, a coolant.

The housing 70 may completely enclose the application 10, or the housing may enclose only a portion of the application 10. For example, the housing may be the crank case or an oil tank on an internal combustion engine, or the housing 70 may be a fluid reservoir in a hydraulic device. The housing 70 may also take other forms.

The moving parts 72 within the housing 70 may be, for example, pistons, valves, and a crankshaft in an internal combustion engine, a piston that moves within a cylinder in a hydraulic device, gears and shafts in a gearbox, a fluid circulation pump in an electrical transformer, as well as other or different moving parts.

The fluid 74 may be an industrial fluid as described above. The fluid is typically contaminated by the operation of the application and, if left untreated, can cause reduced performance of the application 10 and, in some cases, failure of the application 10.

The supply port 76 is an opening through which the fluid leaves the application 10 and is carried via one or more supply lines 14 to the fluid cleaning system 12. Although the illustrated embodiment shows only one supply port 76, the present invention may also be used with two or more supply ports 76.

The return port 78 is an opening through which the fluid returning from the fluid cleaning system 12 returns to the application 10. Although the illustrated embodiment shows only one return port 78, the present invention may also be used with two or more return ports 78.

The fluid cleaning system 12 may operate in the same mode at all times, such as by monitoring one or more parameters of the system 12 and making adjustments to the system 12 to maintain a desired operational state. In other embodiments, however, the system 12 may operate in different modes at different times. For example, the system 12 may be in an operational mode at some times and the system 12 may operate in a diagnostics mode at other times. In other embodiments, the system 12 may have more than two modes of operation, or the system 12 may operate in modes other than those described herein.

Figure 7:
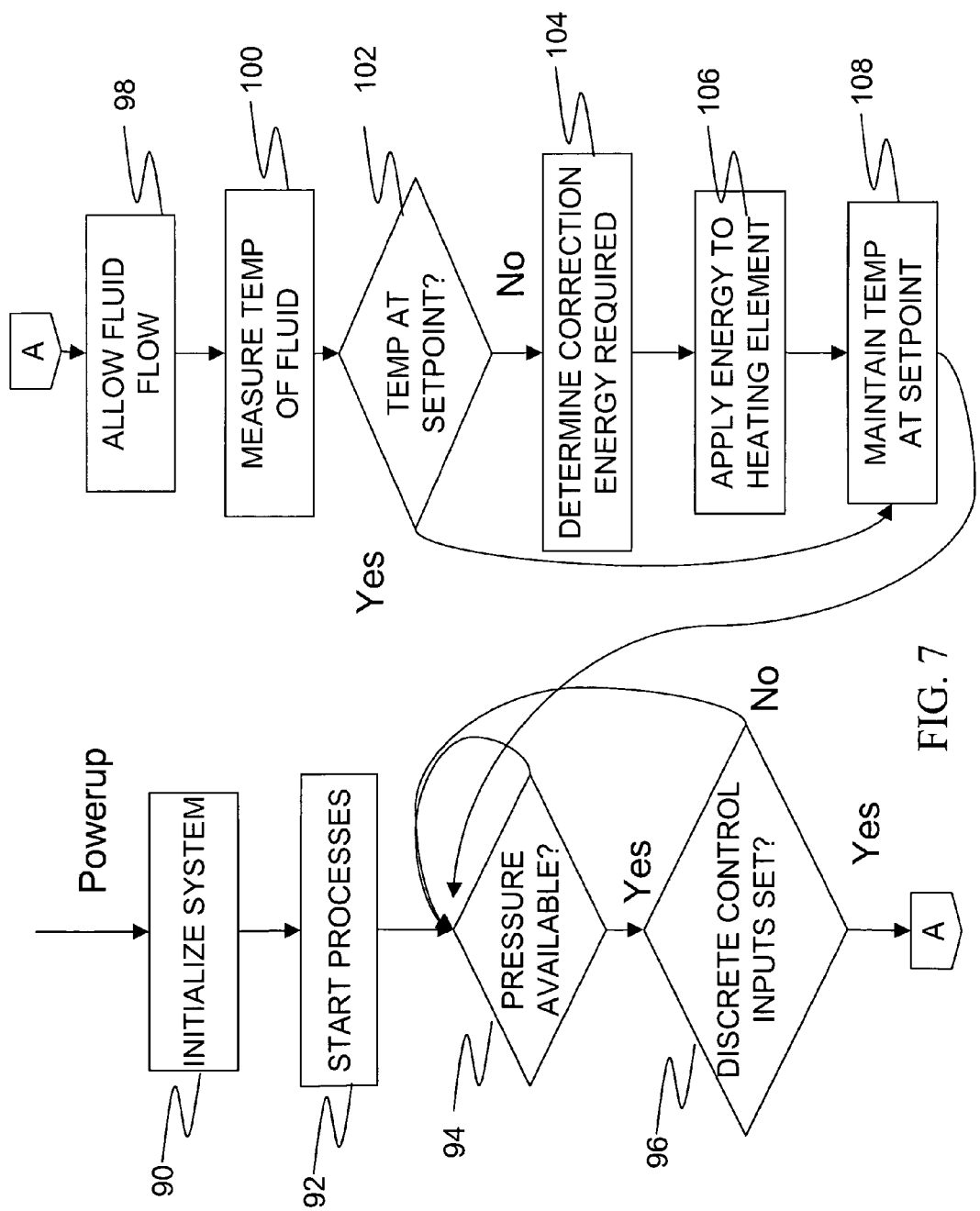
FIGS. 7-9 are flowcharts illustrating different embodiments of modes for the control system of the fluid cleaning system.

FIG. 7 is the flowchart illustrating one embodiment of the operational mode of the system 12 according to the present invention. The operational mode may be, for example, embodied as computer readable instructions which, when executed, cause certain operations to occur. For example, the computer readable instructions may be stored in the memory 52 and executed by the processor 50 to cause the functions of the operation mode to be performed. The operational mode may start on power being applied to the system 12.

Step 90 entitled "Initialize System" performs the task of initializing the processor 50 or electronic control unit. This step 90 may also initialize other processors, such as local controllers 30, 36. For example, this step 90 clears the memory 52, sets up tasks that need to be run periodically or on the occurrence of an event and various other things needed to get the system 12 ready for operation. This step 90 is typically performed when the system 12 is first powered up or when it is restarted. Although not shown in the illustrated embodiment, the present invention may also include a "reset" feature that sends restarts the operational mode by sending it back to step 90.

Step 92 entitled "Start Processes" performs the function of running all the tasks that have been previously setup. These may be, for example, the real time tasks that run in the system 12.

Step 94 entitled "Pressure Available?" performs the function of determining whether there is sufficient fluid pressure available for proper operation. If sufficient pressure is not available, then the system 12 is not ready to start the fluid cleaning operation and will continue to monitor the pressure. If sufficient pressure is available then fluid cleaning may be performed. The pressure may be determined from a sensor 22 in the system 12. The sensor 22 may, for example, be connected to the fluid line 34 near the supply port 32 or at some other location in the system 12 or outside of the system 12. The sensor 22 that monitors the pressure may be, for example, a pressure switch, or a pressure transducer. As an example, pressure may be monitored with the use of a semiconductor based pressure transducer.

Step 96 entitled "Discrete Control Inputs set?" performs the function of checking to see if all the control inputs are set to allow the fluid cleaning function to start. If the inputs are set, then fluid cleaning will be performed. If inputs are not available then fluid cleaning is not performed and the system 12 continues to monitor the states of the inputs. The present invention does not necessary require that all control inputs are set before operation of the system 12. Some control inputs are required for operation, while other control inputs may not be required. In some cases, the absence of certain control inputs may result in certain functionality of the system being disabled, but not result in the system 12 being entirely disabled. Discrete control inputs may be related to many different parts of the system 12 including, for example, control inputs related to fluid level, heating element 26 temperature, temperature in the evaporator 24, fluid flow, and others. The temperature of the fluid at various locations inside the system 12 and outside the system 12 may also be used to generate discrete control inputs, although they may be measured at different locations or in different ways than the measurement of fluid temperature in step 100. The discrete control inputs may be monitored using sensors 22 such as mechanical switches (toggle switches) as well as other devices like Hall effect switches or any other switch that could provide such information.

Step 98 entitled "Allow fluid flow" performs the function of allowing fluid to flow into the cleaning system 12 through one or more fluid flow controllers 40. This may be accomplished, for example, by opening valves acting as fluid flow controllers 40, by turning on pumps acting as fluid flow controllers 40, or by otherwise allowing fluid to flow into the system 12. The fluid flow controllers 40 may be near the supply port(s) 32 or located at other places in the system 12 or outside of the system 12. For example, it is possible to locate the fluid flow controller 40 away from the system 12, such as in or near the application 10 or between the application 10 and the system 12. The fluid flow controller 40 may be implemented, for example, with a solenoid controlled flow device. It may also be controlled using variable flow solenoid valves or variable bleed solenoid valves to allow for finer control of flow. The fluid flow controller 40 may also be implemented with other devices, such as semiconductor-based flow control mechanisms using micro-electro-mechanical systems ("MEMS") technology, as well as other variations. MEMS fluid flow control devices can be purchased, for example, from Micostaq, Inc, 4150 Freidrich Ln # A, Austin, Tex. 78744.

Step 100 entitled "Measure temperature of fluid" performs the function of measuring the temperature of the fluid. The temperature may be measured, for example, with one or more sensors 22 along the fluid lines 34, or with one or more sensors 22 at the filter or the evaporation chamber 24, or at other locations. In one embodiment, the temperature sensor 22 is located within the evaporator 24 so that the temperature of the fluid at or near the heating element 26 can be monitored. The sensor 22 for measuring the fluid temperature may use, for example, an NTC Thermistor, a PTC Thermistor, RTD, semiconductor temperature sensors or a thermocouple. Other types of sensors 22 may also be used to measure temperature of the fluid.

Step 102 entitled "Temperature at setpoint?" performs the function of determining whether the temperature of the fluid is at the setpoint for control. The setpoint may be a particular temperature or a range of temperatures. This is done by comparing the fluid setpoint temperature against the measured fluid temperature from the previous step. If the measured temperature of the fluid is at the fluid temperature setpoint (or within an acceptable temperature range) then a branch to step 108 is made. If it is not, then a branch to step 104 is made. The setpoint temperature may be data stored, for example, in the memory 52.

Step 104 entitled "Compute correction energy required" performs the function of determining the amount of energy required to be applied to the heating element 26 in order to bring the measured temperature of the fluid to the fluid setpoint temperature or temperature range. This step may be performed, for example, by the processor 50 or by a separate device or another processor 50 such as a standard Proportional Controller. Regardless of whether one or more processors 50 are used, this step may be implemented, for example, with the use of PI or PID or Fuzzy logic.

Step 106 entitled "Apply energy to heating element" performs the function of applying the required amount of energy to the heating element 26 in order to bring the measured temperature to the setpoint or temperature range. A pulse width modulated approach may be used to control the energy to the heating element 26. The heating element 26 may be, for example, a resistive type heating element, inductive heating, or other types of heating elements 24.

Step 108 entitled "Maintain temperature at setpoint" performs the function of maintaining the temperature at the desired setpoint value or within a desired temperature range.

The process may be repeated as long as the system 12 is in operation. The present invention is not limited to the illustrated process, and variations to this process and the use of other processes are possible with the present invention.

Steps 90-98 are not necessarily required for the operation of process steps 98-108 which monitor and control the temperature of the industrial fluid. As a result, steps 90-98 may be modified or, in some cases, eliminated. In the later case, the process may begin with step 98, and at step 108 the process may return to step 98. In other embodiments the operational mode may be further simplified such as by omitting step 104 and modifying step 106 so that step 106 increases or decreases energy to the heating element 24 based on the measured temperature and the setpoint, without calculating the energy required to reach the setpoint.

Other variations and modifications of the mode illustrated in FIG. 7 are also possible. For example, the steps may be performed in a sequence other than that illustrated herein, some of the steps may be omitted, and additional steps may be added.

Figure 8:
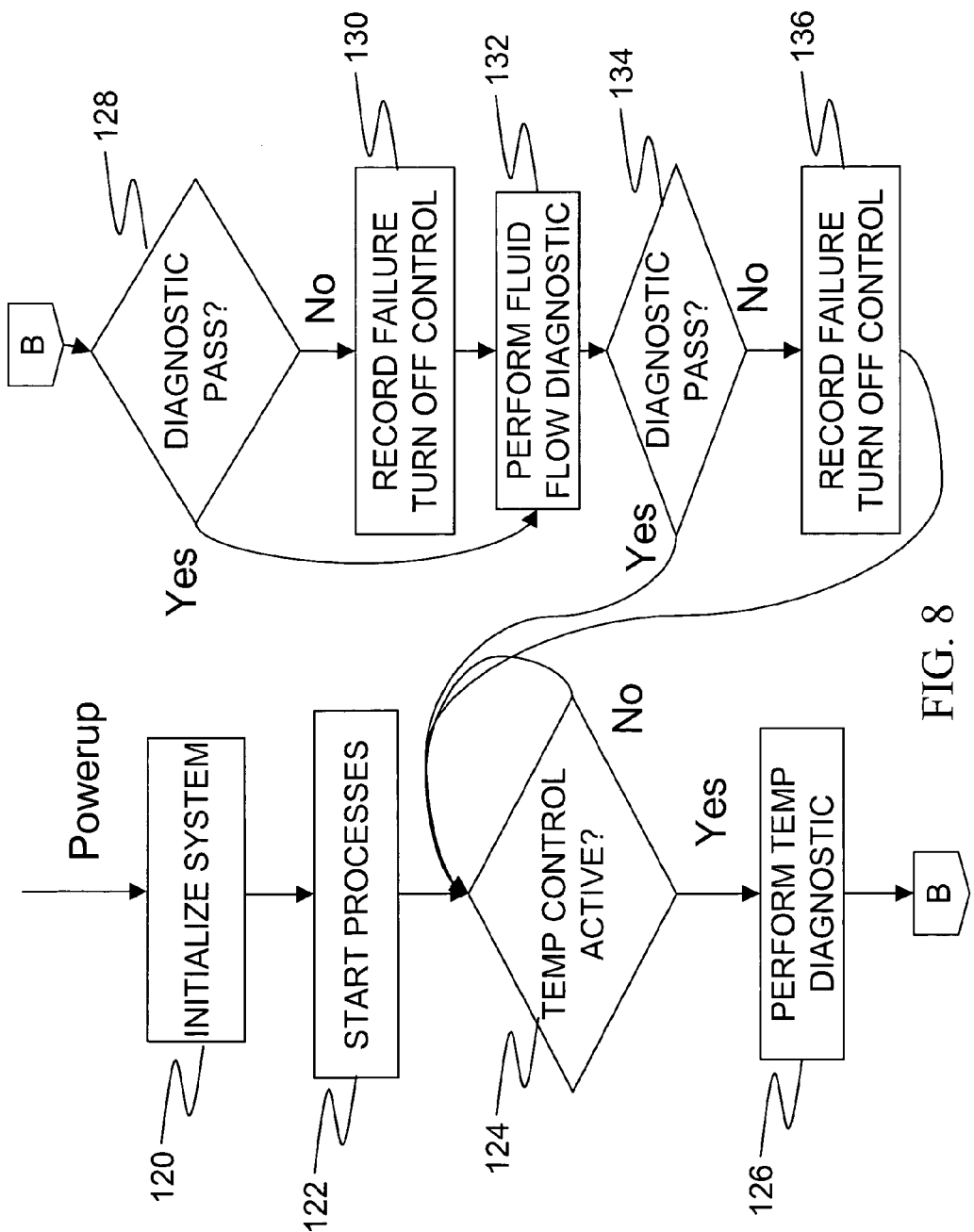

FIG. 8 is the flowchart illustrating one embodiment of the diagnostics mode according to the present invention. The diagnostic mode may be, for example, embodied as computer readable instructions which, when executed, cause certain operations to occur. For example, the computer readable instructions may be stored in the memory 52 and executed by the processor 50 to cause the functions of the diagnostic mode to be performed. The diagnostics mode starts on power being applied to the system 12.

Step 120 entitled "Initialize System" performs the task of initializing the processor 50 or electronic control unit. This step 120 may also initialize other processors, such as local controllers 30, 36. For example, this step 120 clears the memory 52, sets up tasks that need to be run periodically or on the occurrence of an event and various other things needed to get the system 12 ready for operation. This step 120 is typically performed when the system 12 is first powered up or when it is restarted. Although not shown in the illustrated embodiment, the present invention may also include a "reset" feature that sends restarts the operational mode by sending it back to step 120.

Step 122 entitled "Start Processes" performs the function of running all the tasks that have been previously setup. These are all the Real Time tasks that run in a real time fashion.

Step 124 entitled "Temperature Control active?" performs the function of checking to see if the system 12 is currently being controlled for temperature. If it is active then a branch to step 126 is made. If not then step 124 is continuously checked. In the illustrated embodiment the process loops at step 124 until the temperature control is active. In other embodiments, the process may return to another part of the process if the temperature control is not active, and then return to step 124 periodically to see if the temperature control has become active.

Step 126 entitled "Perform Temperature diagnostic" performs the function of checking if the temperature control sub-system is operating correctly. For example, the heating element 26, the heater control logic and drivers 30 (e.g., the local controller 30 for the evaporator 24), and the temperature profiles may be checked by this diagnostic step 126. If any of the above fail the diagnostic check, then it is deemed that the diagnostic has failed.

Step 128 entitled "Diagnostic pass?" performs the function of checking if the diagnostic has passed or failed. If the check passed, then a branch to step 132 is made. If the check failed, then process proceeds to step 130.

Step 130 entitled "Record Failure Turn Off Control" records the failure of the diagnostic test of step 126. This information is stored, for example, in non-volatile memory 52 of the controller 28 and the control of the temperature of the industrial fluid is turned off. In some embodiments, the evaporator 24 include a local controller 30, and the processor 50 may send a control signal to the local controller 30 so that the local controller 30 disables part or all of the functionality of the evaporator 24 that failed a diagnostic test. In some embodiments, an evaporator 24 may fail part, but not all, of a diagnostic test, and the local controller 30 disables part, but not all, of the functionality of the evaporator 24. Thereafter, the process proceeds to step 132.

Step 132 entitled "Perform fluid flow diagnostic" performs the function of running the fluid flow diagnostic. The fluid flow subsystem consists of the fluid flow controller 40, and the fluid flow control logic and fluid flow control drivers 36 (e.g., the local controller 36 for the fluid flow controller 40). If any component of the subsystem fails then the diagnostic fails.

Step 134 entitled "Diagnostic pass?" performs the function of checking if the diagnostic has passed or failed. If the check passed, then a branch to step 124 is made and the diagnostic process is repeated. If the check failed, then the process proceeds to step 136.

Step 136 entitled "Record Failure Turn Off Control" records the failure of the diagnostic test of step 132. This information is stored, for example, in non-volatile memory 52 of the controller 28 and the control of the failed fluid flow controllers 40 are turned off. In some embodiments, the fluid flow controllers 40 include a local controller 36, and the processor 50 may send a control signal to the local controller 36 so that the local controller 36 disables part or all of the functionality of a fluid flow controller 40 that failed a diagnostic test. In some embodiments, a fluid flow controller 40 may fail part, but not all, of a diagnostic test, and the local controller 36 disables part, but not all, of the functionality of the fluid flow controller 40. A branch to step 124 is made to continue the diagnostic process.

Many variations are possible with the diagnostic mode of the present invention. For example, the steps may be performed in a sequence other than that illustrated herein, some of the steps may be omitted, and additional steps may be added. In some embodiments, different parts of the system 12 may be subjected to the diagnostic tests. Furthermore, some embodiments of the system 12 include more than one fluid flow controller 40, more than one evaporator 24, and more than one other components and, as a result, the process illustrated in FIG. 8 may be modified to accommodate multiple components. For example, if the diagnostic of step 132 fails for one fluid flow controller 40, or for one part of a fluid flow controller 40 (e.g., the fluid flow controller 40 has more than one valve or pump, and less than all of the valves or pumps fails), than only the functionality of the failed fluid flow controller 40 or the failed portion of the fluid flow controller 40 may be disabled and recorded in step 136, and the functionality of the other fluid flow controllers 40 or the other portions of the fluid flow controllers 40 may be retained and recorded in step 136. Similar adjustments may be made to the process in order to accommodate multiple heating elements tested in step 126.

Figure 9:
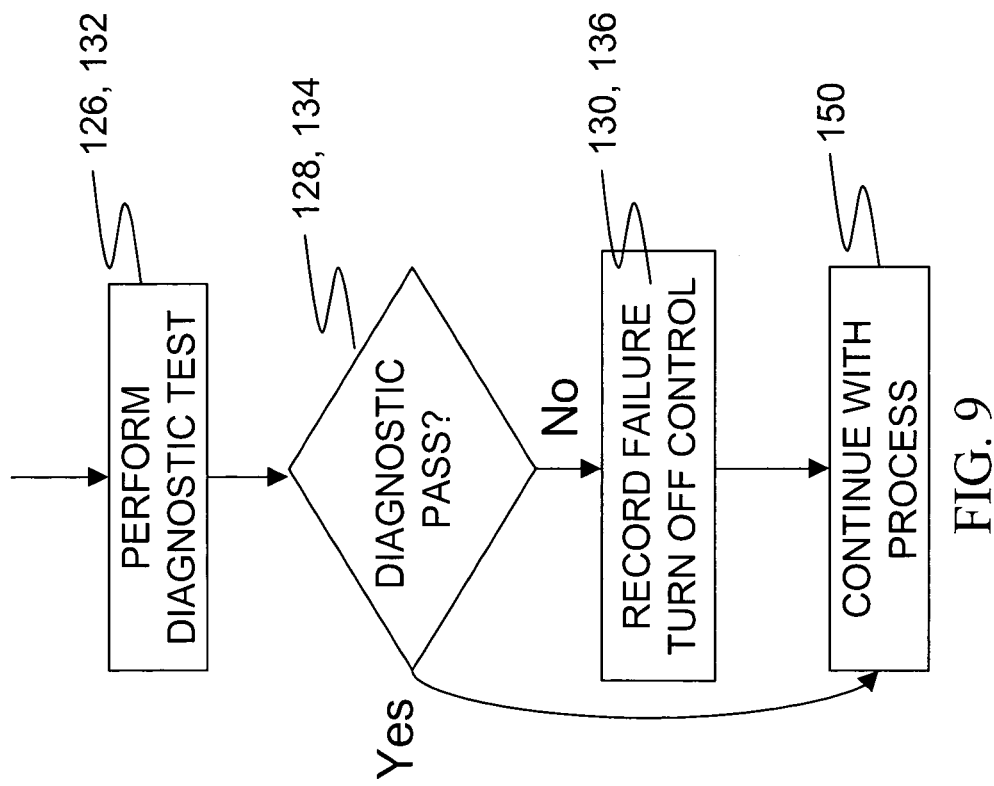

FIG. 9 is a flowchart illustrating a more general example of the diagnostic mode. In that embodiment, the process performs a diagnostic test 126, 132. The diagnostic test may be, for example, a temperature diagnostic, a fluid flow diagnostic (e.g., a valve diagnostic or a pump diagnostic), or some other diagnostic.

Next, the process determines whether the diagnostic test was passed. If it was passed, the process proceeds to step 150 and continues with the process. If the diagnostic test was not passed, the process proceeds to step 130, 136 in which the failure is recorded and in which certain functionality is disabled. As described above, functionality may be partially or entirely disabled. Thereafter, the process continues to step 150.

Step 150 allows for the continuation of the process. Continuation may mean performing more diagnostic tests, proceeding to another mode of operation such as that illustrated in FIG. 7, or some other process.

Figure 10:
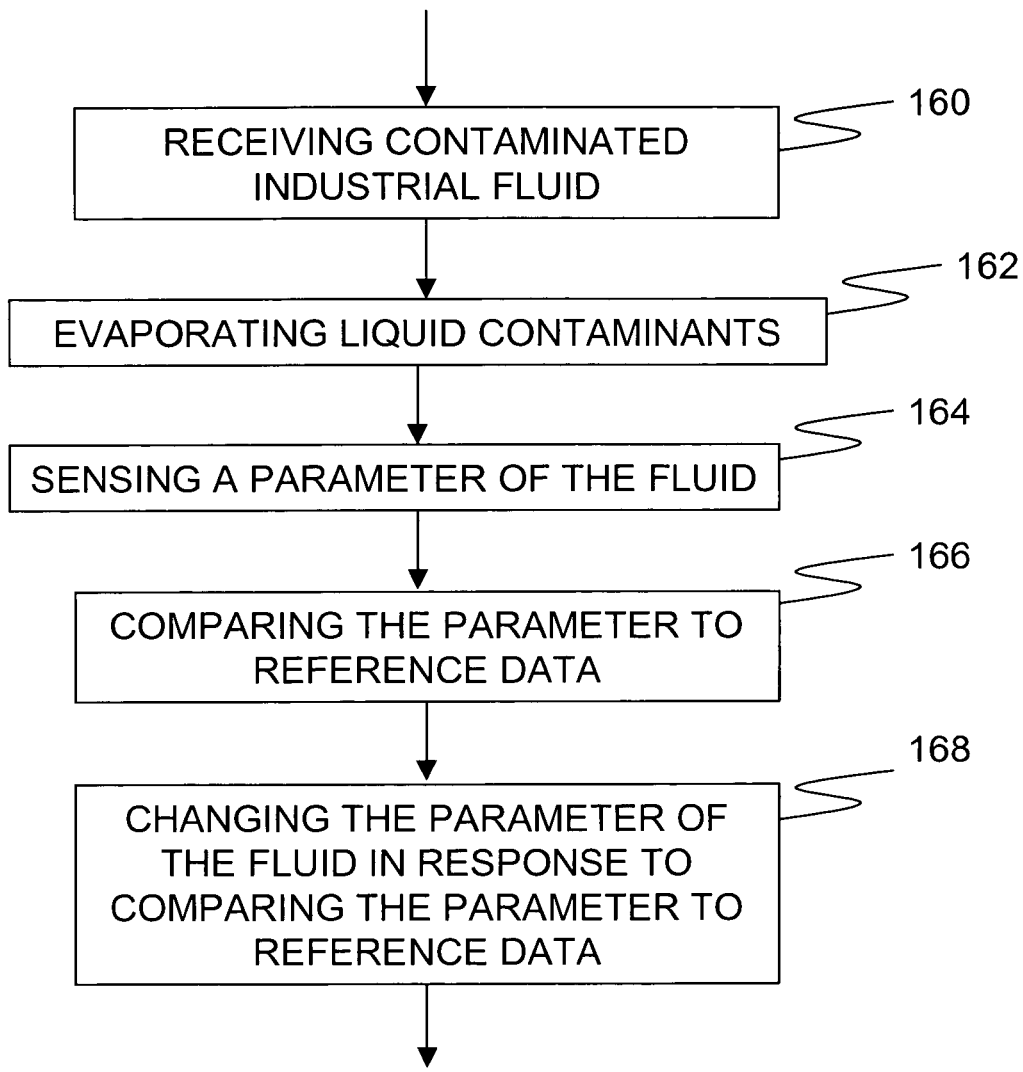
FIGS. 10 and 11 are flowcharts illustrating embodiments of the operation of the present invention.

FIG. 10 is a flowchart illustrating one embodiment of the operation of the present invention.

Step 160 is the system 12 receiving a contaminated industrial fluid. As described above, this may occur with the system 12 and the application 10 being separate devices and the fluid transported between the system 12 and application 10 via supply 14 and return 16 lines, or the system 12 and the application 10 may be integrated and the industrial fluid may be received into the portion of the device the is the fluid cleaning system 12.

Step 162 is the system 12 evaporating liquid contaminants from the industrial fluid. This may be done, for example, with a heating element 26 and evaporator 14 as described above.

Step 164 is sensing a parameter of the industrial fluid. This may be done with one or more sensors 22. The parameter may be fluid temperature, fluid pressure, fluid flow rate, or other parameters.

Step 166 is comparing the parameter of the industrial fluid to reference data. The reference data may be a value, more than one value, a range of values, more than one range of values, or combinations thereof. For example, the parameter may be fluid temperature, and the reference data may be a range of temperatures within which the fluid temperature should fall for desired operation of the system 12.

Step 168 is changing the parameter of the industrial fluid in response to comparing the parameter of the industrial fluid to reference data. For example, if the measured fluid temperature is below the desired temperature of the fluid, then the system 12 may increase the fluid temperature by increasing the energy to the heating element 26, reducing the flow rate of the fluid through the evaporator 24, or other methods of increasing fluid temperature. Many variations are possible for the method according to the present invention. For example, the methods may include additional steps, or variations may be made to the steps illustrated in FIG. 10, or other changes may be made.

Figure 11:
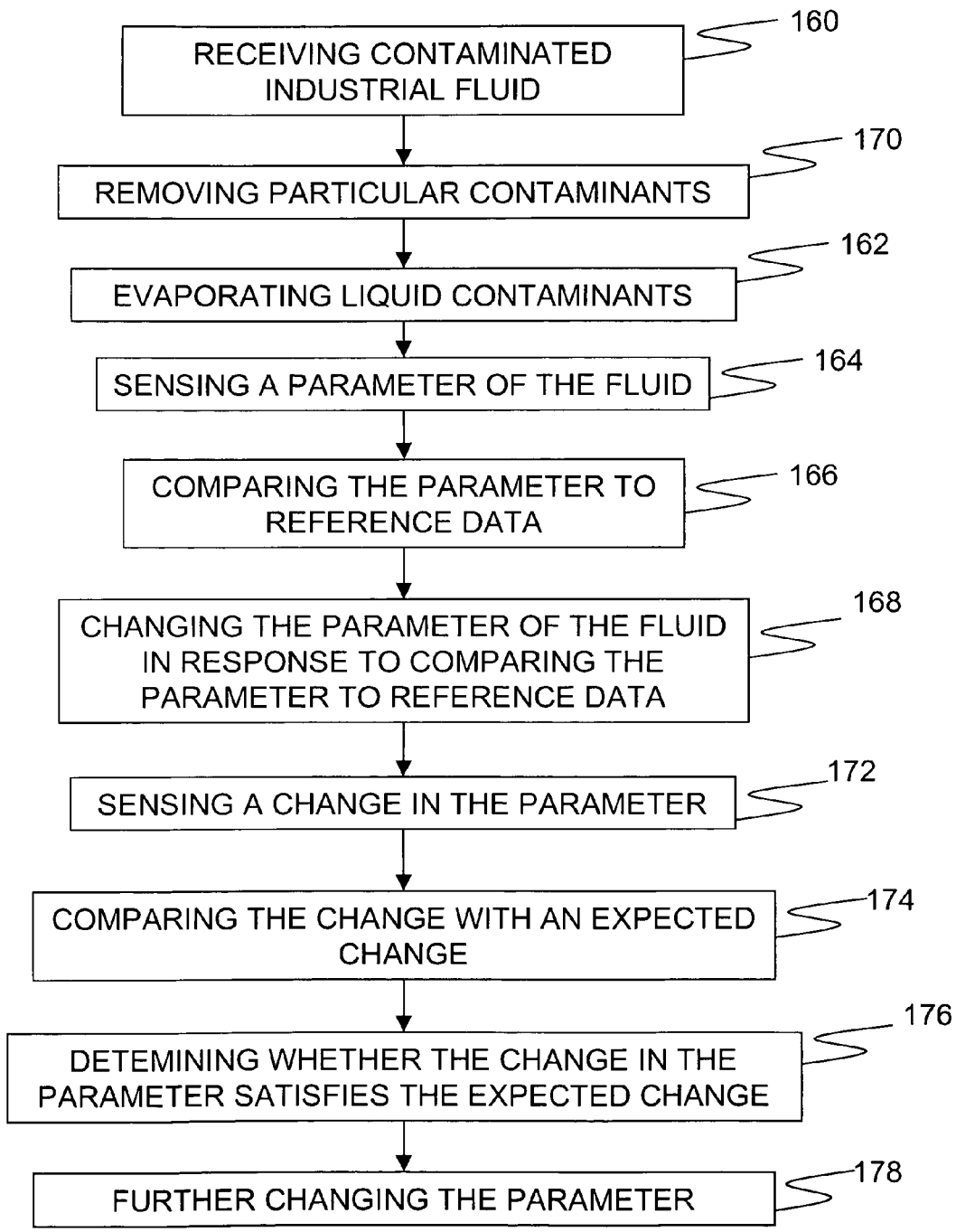

FIG. 11 is a flowchart illustrating another embodiment of the operation of the present invention. In that embodiment, additional steps are included in the process. For example, the method further includes step 170 for removing particulate contaminants from the industrial fluid. This may be accomplished, for example, with a particulate filter 20.

Other modifications and variations are also possible. For example, step 164 may include sensing a parameter selected from a group consisting of: sensing pressure of the industrial fluid, sensing flow rate of the industrial fluid, sensing temperature of the industrial fluid, and sensing fluid level of the industrial fluid. Similarly, the step 166 may include changing the pressure of the industrial fluid, changing the flow rate of the industrial fluid, changing the temperature of the industrial fluid, and changing the fluid level of the industrial fluid.

The present invention may also include, after the step 168 of changing the parameter of the industrial fluid, step 172, sensing a change in the parameter of the industrial fluid, and step 174, comparing the change in the parameter of the industrial fluid with an expected change in the industrial fluid. These steps 172, 174 monitor the effects on the parameter of the industrial fluid with reference to expected changes.

The present invention may also include, after the step 174, the step 176 of determining whether the change in the parameter of the industrial fluid does not satisfy the expected change in the industrial fluid. The present invention may also include the step 178 of further changing the parameter of the industrial fluid if it is determined that the change in the parameter of the industrial fluid does not satisfy the expected change in the industrial fluid. These steps 176, 178 determine whether the desired affect was achieved for the parameter of the industrial fluid and, if necessary, further changes are affected. For example, if the desired temperature change in the industrial fluid was not achieved by increasing the energy to the heating element 26, then the system 12 may further increase the energy to the heating element in order to the further raise the temperature of the industrial fluid, or the system may reduce the fluid flow through the evaporator 24. In this way, the system 12 will continue to work to bring the parameter of interest to the desired value as represented by the reference data.

Figure 12:
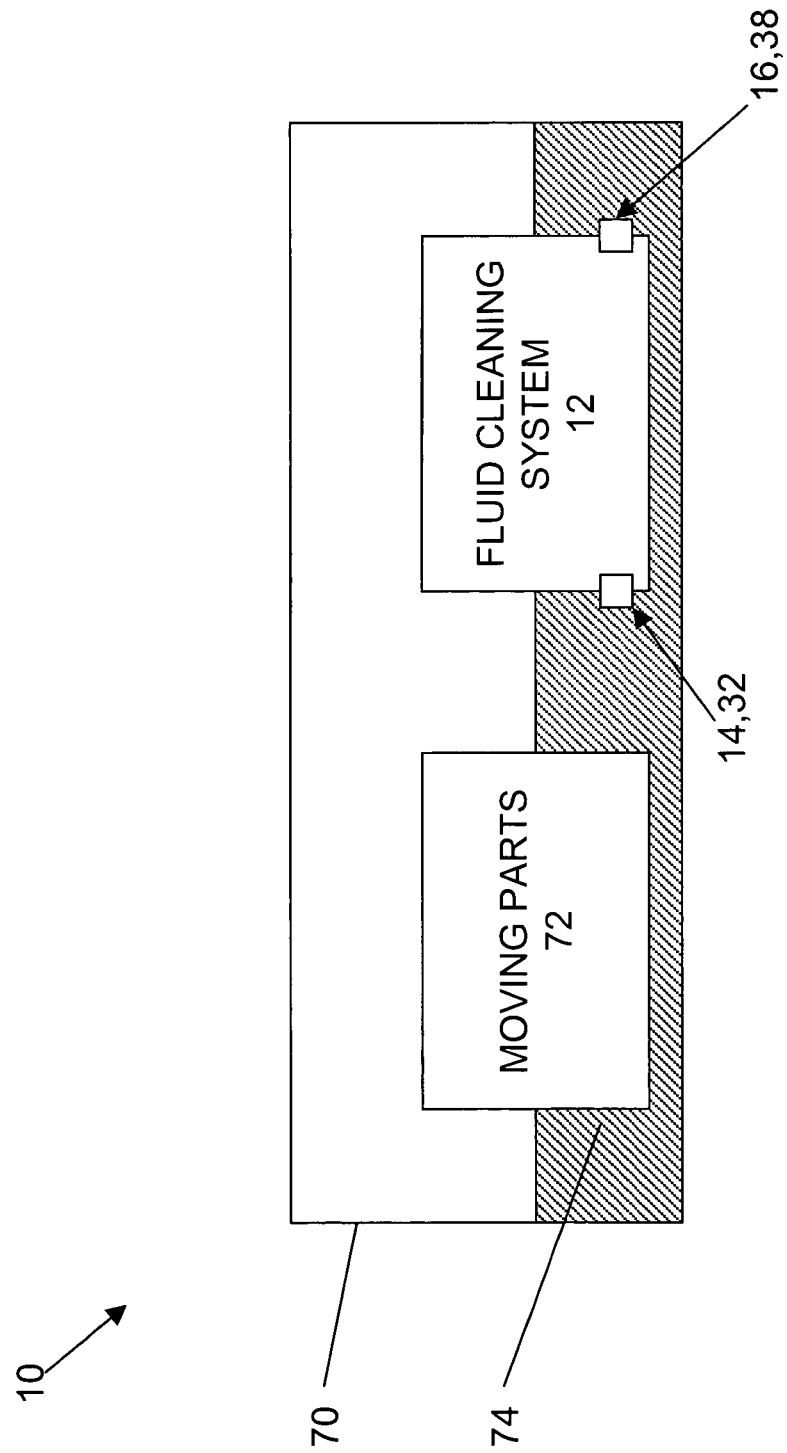
FIG. 12 illustrates an embodiment of an integrated application and system according to the present invention.

FIG. 12 illustrates an integrated application 10 and system 12 according to one embodiment of the present invention. In this embodiment, the system 12 is part of the application 10. For example, the application 10 may be an internal combustion engine and the fluid cleaning system 12 may be located within the oil pan of the internal combustion engine, or within a passage or line that carries the oil or other industrial fluid, or within some other part of the engine by which the industrial fluid is provided to the system 12.

Although the system 12 is shown within the fluid 74, in other embodiments the system 12 may be entirely out of the fluid 74, such as in another part of the application 10 or located above the level of the fluid 74, and the fluid 74 may be moved to and from the system 12 such as with supply 14 and return 16 lines as described above. Also, as discussed above, the application 10 may or may not include moving parts 72.

The illustrated embodiment shows the system 12 including supply 32 and return 38 ports and supply 14 and return 16 lines so that the fluid 74 can enter and leave the system 12. In other embodiments, the system 12 may have no housing or walls to separate it from the application 10. In such an embodiment, there may be no supply and return ports 32, 38 and supply and return lines 14, 16. In other embodiments, the supply and return ports 32, 38 and the supply and return lines 14, 16 may be openings, passages or other fluid passageways between one or more parts of the system 12 and other parts of the application 10.

In one embodiment, the present invention is an apparatus including an application 10 including a housing 70, an industrial fluid 74 within the housing 70, a fluid flow controller 40, and a fluid cleaning system 12. The fluid cleaning system 12 may have many variations as described above. For example, the system 12 may include an evaporator 24, a sensor 22 connected to at least one of the fluid flow controller 40 and the evaporator 24, and a controller 28 connected to an output of the sensor 22. The controller 28 has many variations as described above. For example, the controller 28 may include a processor 50 and a memory device 52 including computer readable instructions which, when executed by the processor cause the processor 50 to perform steps described herein. For example, the steps may be receiving data from the sensor 22, comparing the data from the sensor 22 to reference data stored in the memory device 52, and sending a control signal to at least one of the evaporator 24 and the fluid flow controller 40 based on comparing the data from the sensor 22 to the reference data.

Many other modification and variations are possible with the present invention. For example, the system 12 may include more than one filter 20, evaporator 24, heating element 26; controller 28, supply line and port 14, 32, return line and port 16, 38, processor 50, memory 52, input device 54, output device 56 and other elements. In addition, devices not shown may also be included in the system 12, and some devices shown in the figures (such as the input device 54 and the output device 56) may be combined or integrated together into a single device, or omitted altogether. Also, the relative locations of devices and components may be changed. For example, although it is preferable for the filter 20 to be located upstream from the evaporator 24, it is possible to realize at least some benefits of the present invention by locating the evaporator 24 upstream from the filter 20.

Although the modes of operation in FIGS. 7-9 were described as being performed by the controller 28, the modes may also be operated, in whole or in part, by other processors or controllers, such as the local controllers 30, 36. For example, the local controllers 30, 36 may perform diagnostics on their portion of the system 12 and send results of the diagnostics to the controller 28 for further processing. Alternatively, the local controllers 30, 36 may perform diagnostic tests, make adjustments based on the results of the diagnostic tests, and execute the adjustments either with or without receiving control signals from the controller 28. Other variations are also possible.

Furthermore, although the present invention has generally been described in terms of fluid cleaning, and in terms of specific embodiments and implementations, the present invention is applicable to other methods, apparatuses, systems, and technologies. For example, the present invention has other uses in the automotive sector as well as many more in other markets including manufacturing, medical, and the food and beverage industry. Fluids that could benefit include transmission and brake fluids, cooling fluids, processing chemicals, cleaning agents, and cutting fluids. In addition, the examples provided herein are illustrative and not limiting. Those and other variations and modifications of the present invention are possible and contemplated, and it is intended that the foregoing specification and the following claims cover such modifications and variations.

The invention claimed is:

1. A system, comprising an internal combustion engine, an industrial fluid, and a fluid cleaning system, wherein
the industrial fluid comprises a lubricating oil;
the fluid cleaning system comprises
a fluid flow controller comprising at least a pump for controlling the flow of fluid through the fluid cleaning system;
a fluid cleaning system fluid supply port with a supply line connecting the fluid cleaning supply port to a supply port of the internal combustion engine;
a fluid cleaning system fluid return port with a return line connecting the fluid cleaning return port to a return port of the internal combustion engine;
a fluid filter for removing particulate contaminants;
an evaporator containing a heating element for evaporating liquid contaminants from the fluid;

a fluid line connecting the evaporator between the fluid cleaning system fluid supply port and the fluid cleaning system fluid return port;
sensors to detect various operating characteristics within the fluid cleaning system wherein at least one sensor is connected to the fluid flow controller, at least one sensor is connected to the evaporator, and at least one sensor is connected to the fluid line;
a central controller connected to an output of the sensors, wherein the central controller includes a processor and
   a memory device including computer readable instructions which, when executed by the processor cause the processor to perform the steps of:
receiving data from the sensors;
comparing the data from the sensors to reference data stored in the memory device;
sending a control signal to at least the evaporator and the fluid flow controller based on comparing the data from the sensors to the reference data;
wherein said central controller monitors the temperature of the fluid in the evaporator and said computer readable instructions include computer readable instructions that cause the processor to perform the steps of measuring a temperature of the industrial fluid in the evaporator,
determining whether the temperature of the industrial fluid is at a setpoint,
determining an amount of energy required to be applied to the heating element in the evaporator to bring the temperature of the industrial fluid to the setpoint, then applying the amount of energy required to be applied to the heating element to bring the temperature of the industrial fluid to the setpoint.

2. The system of claim 1, wherein when determining whether the temperature of the industrial fluid is at a setpoint, the setpoint is a temperature range.

3. The system of claim 1, wherein when determining whether the temperature of the industrial fluid is at a setpoint, the setpoint is a temperature.

4. A fluid cleaning system for cleaning a contaminated lubricating oil from an internal combustion engine, comprising:

a fluid flow controller comprising at least a pump for controlling the flow of lubricating oil through the fluid cleaning system;
a fluid supply port, connectable through a supply line to a fluid supply port of an internal combustion engine, for receiving contaminated lubricating oil;
a fluid return port, connectable through a return line to a fluid return port of an internal combustion engine, for providing a cleaned lubricating oil;
a fluid filter for removing particulate contaminants;
an evaporator containing a heating element for evaporating liquid contaminants from the-fluid lubricating oil;
a fluid line connecting the evaporator between the fluid supply port and the fluid return port;
sensors to detect various operating characteristics within the fluid cleaning system wherein at least one sensor is connected to the fluid flow controller, at least one sensor is connected to the evaporator, and at least one sensor is connected to the fluid line;
a central controller connected to an output of the sensors, wherein the central controller includes:
a processor and
a memory device including computer readable instructions which, when executed by the processor cause the processor to perform the steps of:
receiving data from the sensors; comparing the data from the sensors to reference data; sending a control signal to at least the fluid flow controller and the evaporator based on comparing the data from the sensors to the reference data;
wherein said central controller monitors the temperature of the fluid in the evaporator and said computer readable instructions include computer readable instructions that cause the processor to perform the steps of measuring a temperature of the lubricating oil in the evaporator, determining whether the temperature of the lubricating oil is at a setpoint, determining an amount of energy required to be applied to the heating element to bring the temperature of the lubricating oil in the evaporator to the setpoint, then applying the amount of energy required to be applied to the heating element to bring the temperature of the lubricating oil to the setpoint.

* * * * *